United States Patent [19]
Demarest et al.

[11] Patent Number: 5,920,482
[45] Date of Patent: Jul. 6, 1999

[54] METHODS AND SYSTEMS FOR VARYING PARAMETERS AT A NEEDLE SWAGING STATION

[75] Inventors: David D. Demarest, Parsippany; Michael G. Hodulik, Dunellen, both of N.J.; Timothy P. Lenihan, Morrisville, Pa.; Loy William Shreve, II, San Angelo, Tex.

[73] Assignee: Ethicon, Inc., Somerville, N.J.

[21] Appl. No.: 08/804,475

[22] Filed: Feb. 21, 1997

[51] Int. Cl.$^6$ .................................................. G01N 3/10
[52] U.S. Cl. ............................. 364/474.01; 364/472.01; 364/474.02; 364/468.24; 73/827; 73/833
[58] Field of Search ........................ 364/470.1, 474.01, 364/472.01; 318/432; 57/80; 242/412, 413.3, 414.1, 418.1, 421.7, 520, 159; 73/827

[56] References Cited

U.S. PATENT DOCUMENTS

| | | | |
|---|---|---|---|
| 4,160,360 | 7/1979 | Carvalho | 57/81 |
| 4,347,993 | 9/1982 | Leonard | 242/75.51 |
| 5,269,808 | 12/1993 | Proto | 606/228 |
| 5,487,216 | 1/1996 | Demarest | 29/705 |
| 5,623,189 | 4/1997 | Hemmer | 318/432 |

*Primary Examiner*—James P. Trammell
*Assistant Examiner*—Demetra R. Smith

[57] ABSTRACT

Methods and procedures for varying parameters at a work station where different size and/or type needles are automatically sutured to different size and/or type sutures, such as: a method and system for applying a predetermined, given tension to different size and/or type sutures; a system and method for inserting a suture into different size and/or type needles to a predetermined, given depth; and a method and system to cool different size and/or type sutures for a predetermined, given length of time. Values for these parameters may be stored in a supervisor computer and then transmitted to controllers to operate the work station with these parameter values for each of a plurality of different size and/or type sutures and/or needles.

24 Claims, 8 Drawing Sheets

METHODS AND SYSTEMS FOR VARYING PARAMETERS AT A NEEDLE SWAGING STATION

BACKGROUND OF THE INVENTION

This invention generally relates to systems and methods for varying parameters at work stations where needles are swaged to sutures. More specifically, the present invention relates to such systems and methods that are well suited for automatically adjusting those parameters in response to operator input commands.

Machines have recently been developed that automatically suture, swage and package surgical needles; and, for example, such machines are disclosed in U.S. Pat. Nos. 5,494,420, 5,487,216 and 5,487,212. Generally, in the operation of these machines, unsutured needles are fed to the machines, and an indefinite length of suture, taken from a spool or similar supply, is inserted into a recess or opening in the needle. The needle is swaged in the area of that recess or opening to secure the connection between the suture and the needle, the suture is cut to a preset length, and the needle, or a group of such needles, is then packaged. In this process, the suture is typically held in tension while it is inserted into the needle. This tension helps to insert the suture properly into the needle and also helps to insure that the suture is neatly cut.

These machines have proven to be highly valuable, and they effectively produce large numbers of excellent quality, packaged, sutured needles. Moreover, these needles are produced very economically on a large scale, high speed, mass production basis.

Usually, these machines are used, at different times, with different sizes and types of needles and with different sizes and types of suture. When the needle or suture type or size is changed, a number of adjustments are made to the machines. For example, these adjustments may include changing the tension applied to the suture as it is inserted into the needle. Normally, these adjustments are done by hand, which can be a time consuming process.

SUMMARY OF THE INVENTION

An object of this invention is to improve methods and systems for varying parameters at a work station where needles are automatically sutured.

A further object of this invention is to improve methods and systems for applying and adjusting the tension on a suture in a needle suturing assembly.

Another object of the present invention is to apply a variable torque to a tension roller, which is used to develop tension on a suture in a needle suturing assembly, and to change that torque, to thereby adjust the tension developed on the suture, without requiring any manual adjustment of the tension roller.

A further object of this invention is to provide a motor, and a procedure for controlling that motor, for controlling and adjusting the tension applied by a tension roller on a suture in a needle suturing assembly.

A further object of the present invention is to improve methods and systems for adjusting the depth to which a suture is inserted into a needle.

Still another object of this invention is to improve methods and systems for adjusting the length of time a suture is cooled at an automated needle suturing work station.

These and other objects are obtained with methods and procedures for varying parameters at a work station where needles are automatically sutured. In accordance with one aspect of the invention, a method and system are provided for applying a predetermined, variable tension to a suture. This system includes a rotatable roller for engaging the suture, and a variable torque device connected to the roller to apply a variable torque thereto to resist rotation of the roller to apply tension to the suture. The system further includes a control subsystem including means to identify a given torque level, and a controller to operate the variable torque device to apply said given torque level to the roller.

In accordance with another aspect of the invention, a system and method are provided for inserting a suture into a needle to a predetermined, variable depth. This system comprises a gripper assembly for holding the suture, and moving means connected to the gripper assembly to move that assembly a variable, controlled distance to insert the suture into the needle. This system also includes a control subsystem including means to identify a given depth, and a controller to operate the moving means to move the gripper assembly to move the suture to that given depth in the needle.

With a third aspect of the invention, a method and system are provided to cool a suture for a predetermined, variable length of time. This system includes means to heat the suture for a preset length of time, and means to move the suture to a predefined location, after that preset length of time and while the suture cools. The system also includes a control subsystem including means to identify a given length of time; and a controller to operate the moving means, and to delay operation of that moving means for that given length of time, to increase the amount of time the suture cools before reaching the predefined location.

Further benefits and advantages of the invention will become apparent from a consideration of the following detailed description, given with reference to the accompanying drawings, which specify and show preferred embodiments of the invention.

DETAILED DESCRIPTION OF THE PREFERRED EMBODIMENTS

Figure 1:
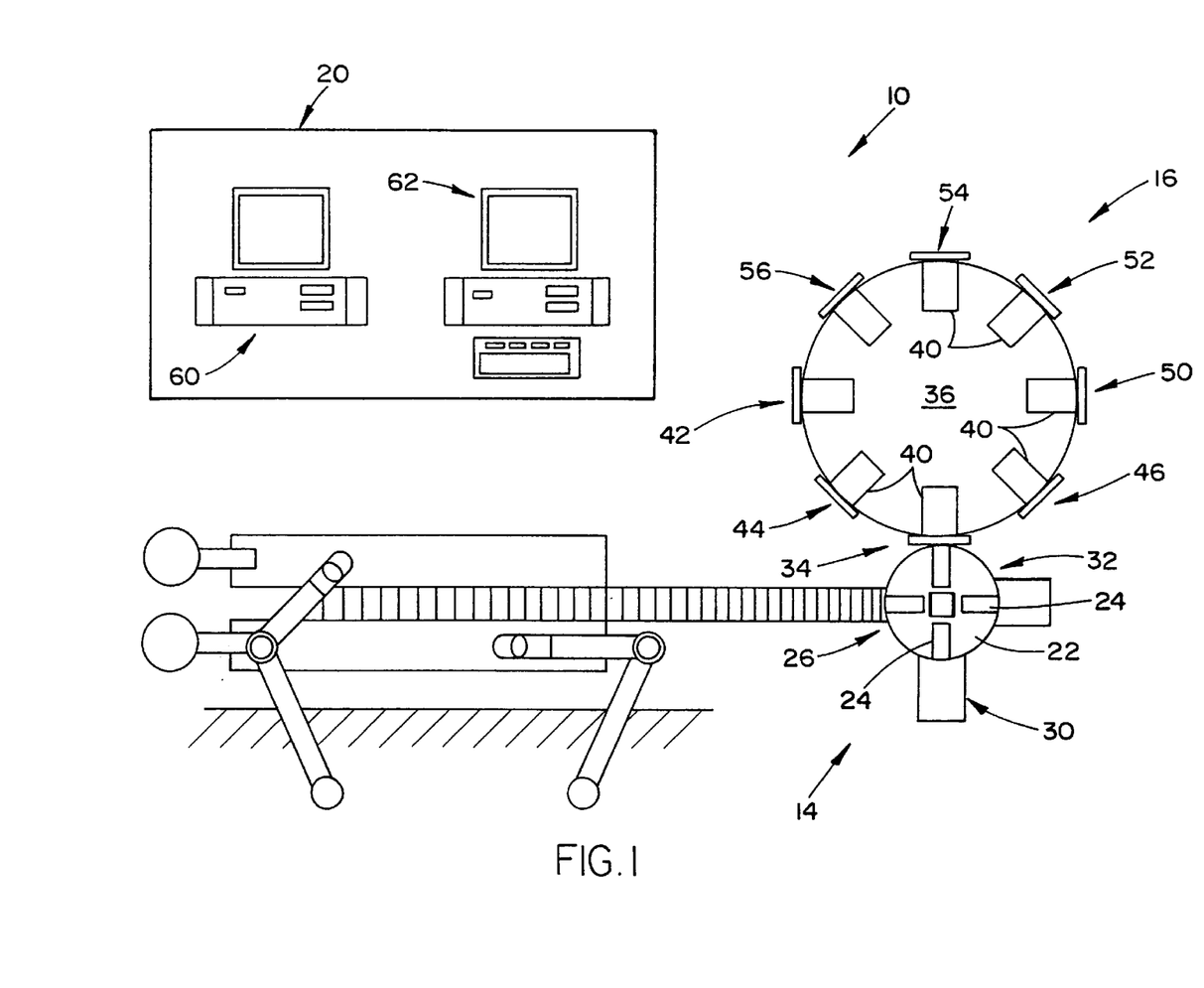
FIG. 1 shows an automated needle suturing and packaging machine.

FIG. 1 shows machine 10 for automatically threading, swaging and packaging surgical needles, and this machine comprises needle sorting and conveying mechanism 14, needle suturing and swaging mechanism 14, packaging mechanism 16, and control system 20. Mechanism 12 includes a rotatable dial or plate 22, a multitude of needle grippers 24 mounted on the plate, and a multitude of work stations 26, 30, 32 and 34 located around that dial or plate. Similarly, mechanism 16 includes a rotatable dial or plate 36, a multitude of package nests 40 mounted thereon, and a multitude of work stations 42, 44, 34, 46, 50, 52, 54 and 56 located around the dial or plate. Control system 20 preferable includes operator computer 60 and supervisor computer 62.

Figure 2:
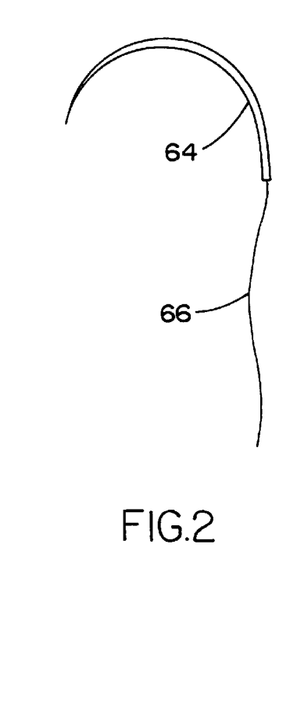
FIG. 2 shows a needle that has been sutured on the machine of FIG. 1.

Machine 10 may be used with a variety of types and sizes of needles. As an example, FIG. 2 shows a needle that has been sutured and swaged on the machine, with the needle and the suture being referenced at 64 and 66 respectively.

Generally, in the operation of machine 10, mechanism 12 sorts, singulates and conveys precisely oriented surgical needles to needle grippers 24 on rotary dial 22. That dial then rotates, in the counterclockwise direction as viewed in FIG. 1, to move or index, the needles to and through work stations 26, 30, 32 and 34 to suture and swage the needles. At work station 34, the needles are transferred from dial 22 to dial 36, which then rotates, also in the counterclockwise direction as viewed in FIG. 1, to move, or index, the needles to and through work stations 46, 50, 52, 54 and 56 to package the needles.

In the operation of machine 10, a plurality or a multitude of needles, such as eight needles, are placed in each needle package on packaging mechanism 16; and because of this, dial 22 is indexed or moved a plurality of times such as eight times, each time dial 36 is moved or indexed. Moreover, in the operation of machine 10, operations are performed simultaneously at all of the work stations of the machine. In particular, during a given work cycle of mechanism 14, operations are performed at each of the work stations 26, 30, 32 and 34; and once those operations are completed, rotary dial 22 rotates to move the needles to the next work station. Similarly, during a given work cycle of mechanism 16, operations are performed at each of the work stations 42, 44, 34, 46, 50, 52, 54 and 56; and once these operations are completed, rotary dial 36 rotates to move the package to the next work station.

More specifically, at station 26, grippers 24 on dial 22 receive the needles, one at a time, from mechanism 12. Station 30 is an automatic swaging station, where suture material is inserted into the needle, swaged thereto, and cut; and station 32 is a pull test station, where the sutured needles, referred to as armed needles, are pull tested to determine whether certain minimum and/or maximum pull test requirements are met. Station 34 is a transfer station, where the armed surgical needles are transferred to a package tray mounted on rotary plate 36.

Station 42 of needle packaging mechanism 16 is a package load station, where empty package trays are fed onto a receiving nest; and station 44 is a package detect station, where a check is made to determine whether the package tray has in fact been mounted on the tool nest. Station 34 is, as mentioned above, a load station, where the armed needles are transferred from mechanism onto the package tray; and station 46 is a needle check station, where a check is made for missing needles.

Station 50 is a suture winding station where the trailing ends of the sutures of the armed needles are gathered and wound around the package tray; and station 52 is a manual inspection station, where a manual inspection may be made of the work in progress. At station 54, a cover is applied to the package tray; and at station 56, the package is removed from the machine 10. The removed package may be further processed, or if the package has been found defective, the package may be discarded.

Figure 3:
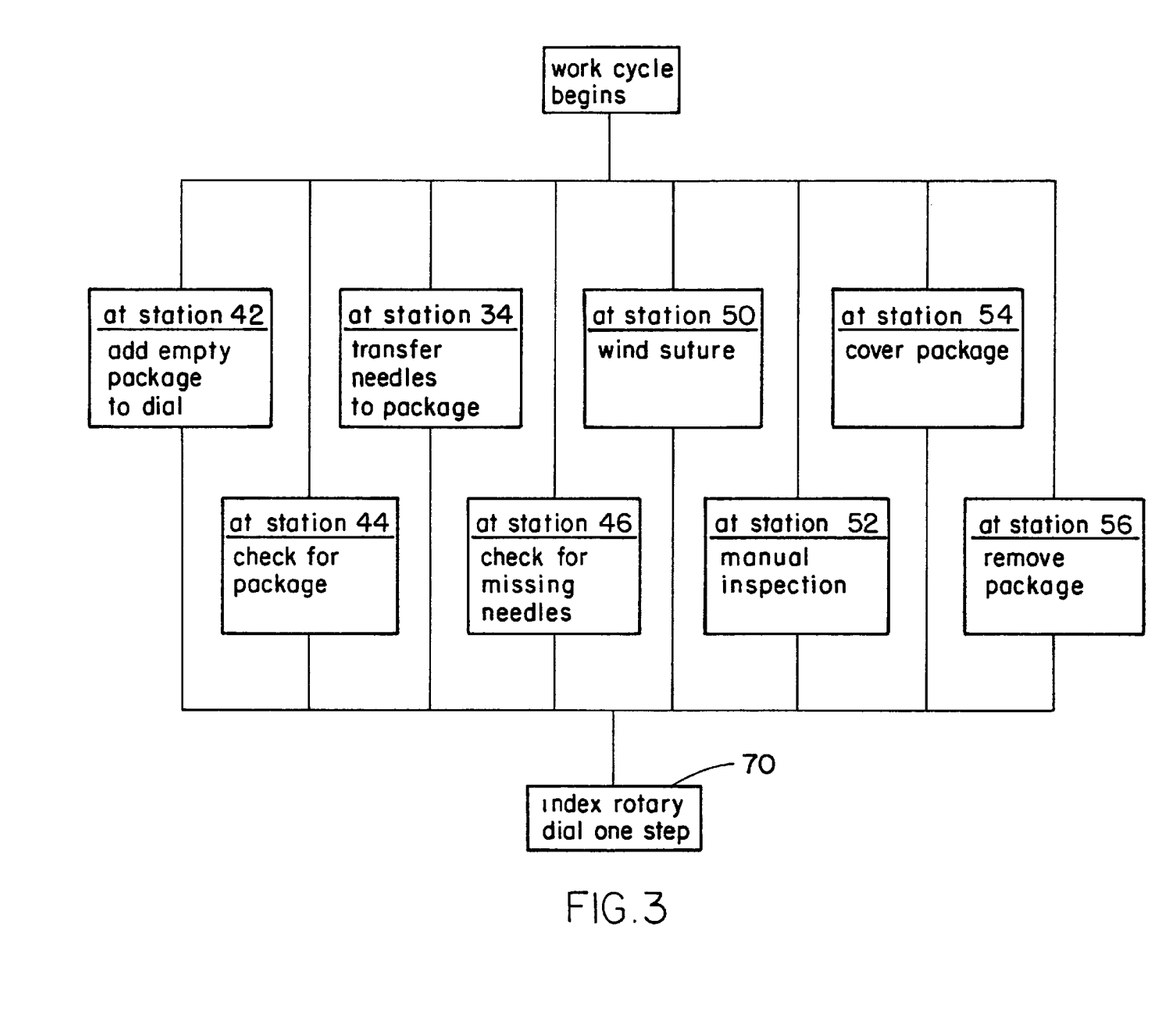
FIG. 3 is a flow chart illustrating the general operation of a packaging mechanism of the machine.

The above-described operation of mechanism 16 is illustrated in the flow chart of FIG. 3. With reference to this Figure, at step 70, the control system 20 will determine whether rotary dial 22 has been indexed the number of times needed to place the desired number of needles in the package on dial 36 at work station 34. Once this is done, and once the operations performed at the work stations of mechanism 16 are completed, rotary dial 36 rotates approximately 45 degrees to move each package to the next work station and to move an empty package nest to work station 42.

Control system 20 helps to supervise, control and coordinate the operations of mechanisms 12, 14 and 16. More specifically, supervisor computer 62 may be provided with various data bases, referred to as batch recipes, that contain lists of values for parameters on machine 10. Computer 62 may have a respective one batch recipe for each type of needle that may be used on machine 10; and when needles of a given type are fed to the machine, the associated batch recipe is invoked to set parameters on the machine. Also, supervisor computer 62 may hold data or status words that in turn hold bits or flags describing various conditions on machine 10. Some of these status words may indicate conditions at the work stations on the machine, and other status words may describe the conditions of the needles or of the packages at these stations.

Operator computer 60 acts as an interface between an operator and supervisor computer 62 for receiving input data and commands from the operator and for displaying data and messages to the operator. The operator computer also acts as an interface between the operator and sorting mechanism 12, suturing mechanism 14, and packaging mechanism 16.

Any suitable sorting and conveying mechanism, and any suitable suturing and swaging mechanism may be used in machine 10. Likewise, machine 10 may have any appropriate packaging mechanism and control system. Mechanisms and control systems that may be used in machine 10 are disclosed, for example, in U.S. Pat. Nos. 5,568,593, 5,495, 420, 5,487,216, and 5,487,212, the disclosures of which are herein incorporated by reference.

Figure 4:
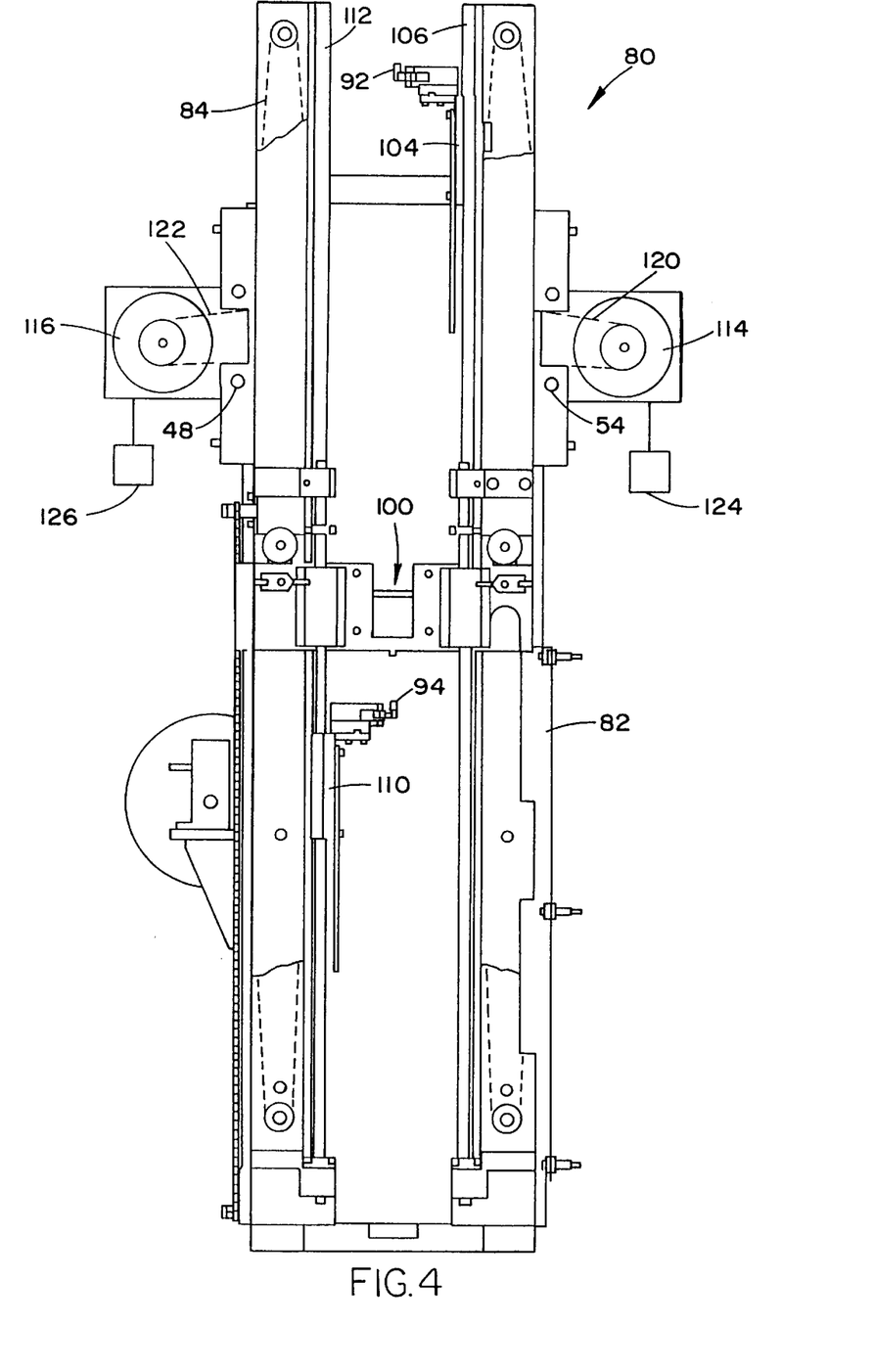
FIG. 4 and 5 illustrates a needle suturing station of the machine shown in FIG. 1.
Figure 5:
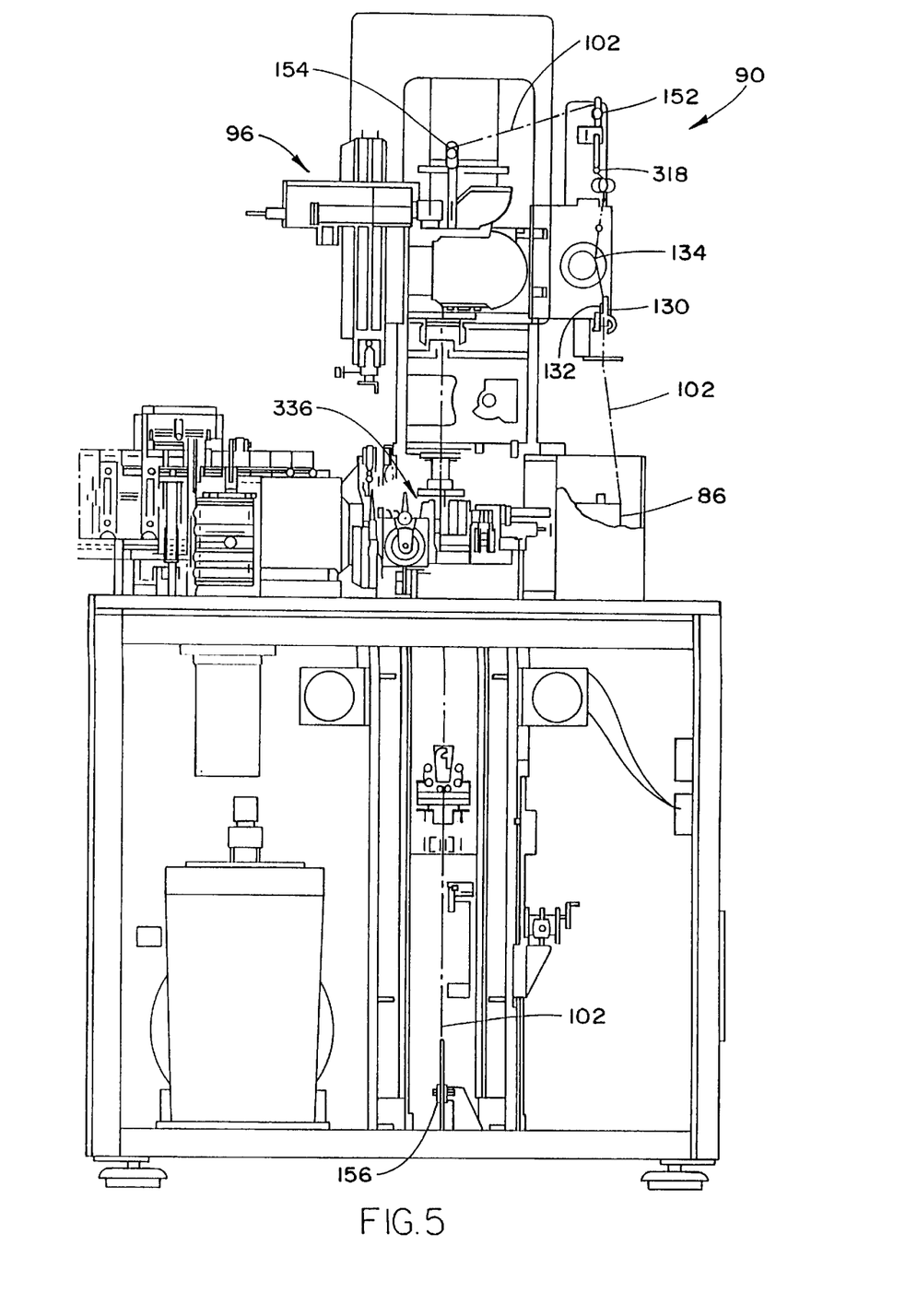

The present invention relates to setting and varying parameters at swaging station 30, which is shown in greater detail in FIGS. 4 and 5. With reference to these FIGs, this work station comprises a frame 80 having parallel longitudinal members 82 and 84 that define a longitudinal drawing axis, a suture supply 86, and a tension mechanism 90. This work station further comprises a pair of grippers 92 and 94, a tipping assembly 96 and a cutting assembly 100. Swaging station 30 and components thereof are described in detail in copending U.S. patent application Ser. Nos. 08/512,962, 08/804,478, 08/803,573, and 08/804,477 entitled "Suture Cutting System," the disclosures of which are incorporated herein by reference.

Generally, in the operation of the work station 30, an indefinite length of suture 102 is pulled off one end of a supply roll 86 and through the tensioning mechanism 90, which is used to develop tension in the suture. The suture is then passed around a series of pulleys that align the suture with the drawing axis of frame 80. Grippers 92 and 94 are mounted on longitudinal members 82 and 84 for sliding movement therealong, and these grippers are used alternately to grip the suture 102, to draw it along the drawing axis and to insert the suture into a needle. Cutting assembly 100 is used to sever the indefinite length of suture to provide uniform lengths of suture; and tipping assembly 96 is provided to stiffen the areas of the suture that are subsequently cut, and this stiffening is accomplished by heating and then cooling those areas.

More specifically, right gripper 92 is mounted on right carrier 104; and this carrier is supported for reciprocating sliding movement along right guide rod 106, which in turn is parallel to and connected to right side member 82. Similarly, left gripper 94 is mounted on left carrier 110; and this carrier is supported for reciprocating sliding movement along left guide rod 112, which is parallel and connected to left side member 84. Each of the grippers 92 and 94 has open and closed, or gripping, positions. In the gripping position, the gripper holds a suture; while in the open position, the gripper may be moved down along the drawing frame 80 without interfering with upward movement of the other gripper.

The right gripper 92 and gripper carrier 104 are driven by right servo motor 114, which is mounted to the right side rail 82 by a bracket; and similarly, the left gripper 94 and gripper carrier 110 are driven by a left servo motor 116, which is mounted to the left side rail 84 by a bracket. Right servo motor 114 drives timing belt 120, which is clamped to right gripper carrier 104, thereby enabling vertical positioning of the right gripper carrier and the right gripper; and left servo motor 116 drives timing belt 122, which is clamped to left gripper carrier 110, thereby enabling vertical positioning of the left gripper carrier and the left gripper. In the preferred embodiment, both left and right servo motors are interfaced with and controlled by programmable logic units, schematically represented in FIG. 4 at 124 and 126, and as generally explained in U.S. Pat. No. 5,487,216.

Figure 6:
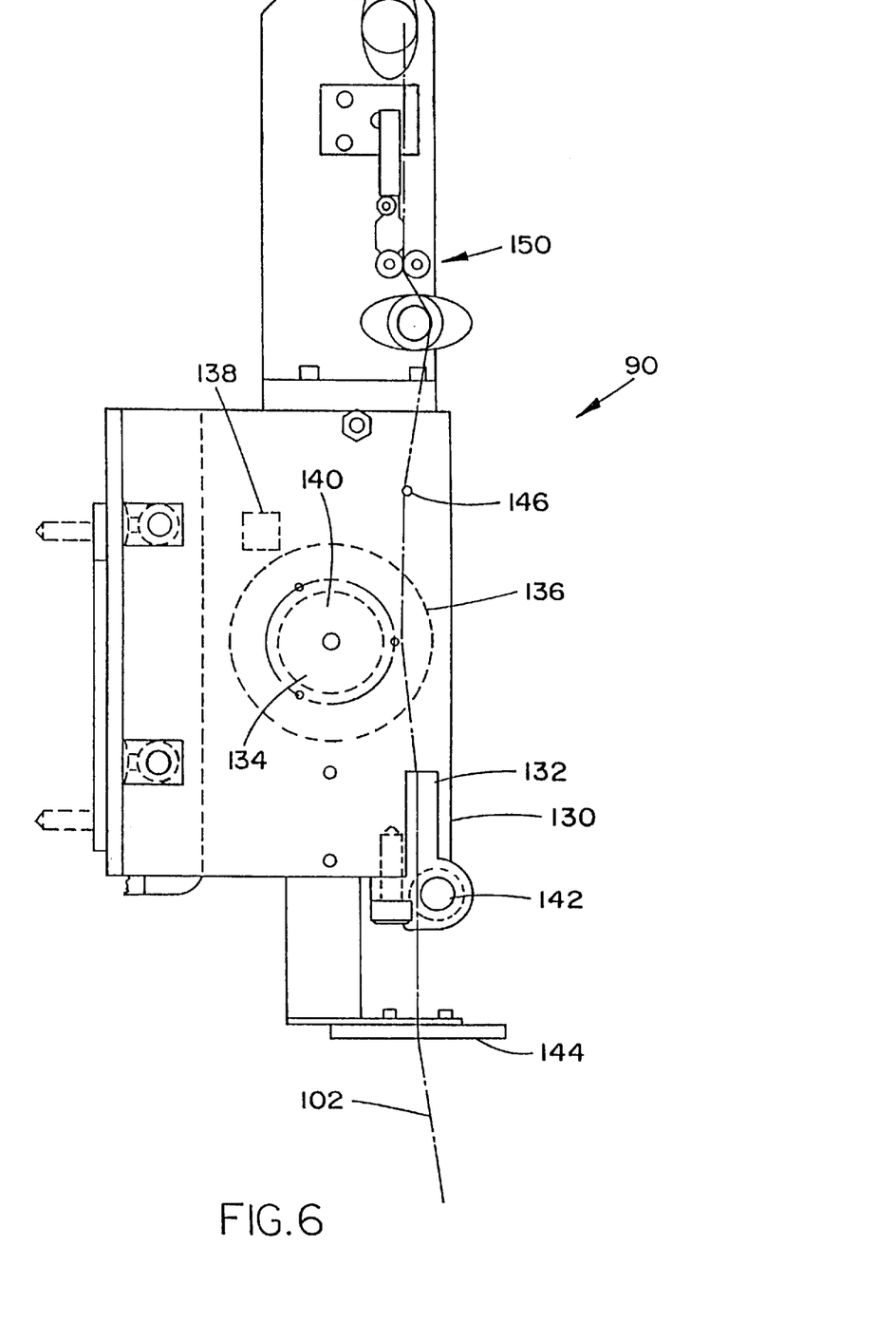
FIG. 6 shows a suture tensioning mechanism of the suturing station.

Tensioning assembly 90 of work station 30 is illustrated in greater detail in FIGS. 5 and 6; and this assembly includes stationary guide frame 130, pivotal guide frame 132, tension roller 134, torque motor 136, motor controller 138 and motor brake 140. Pivotal guide frame 132 is pivotally mounted about a pin 142 at the lower end of the stationary guide frame 130. Each of the frames 130 and 132 has a series of spaced guide elements, each of these guide elements has a central guide aperture, and the guide elements of frames 130 and 132 are interleaved such that the guide elements of frame 130 alternate with the guide elements of frame 132.

Suture 102 extends through the center of annular guide disc 144 and then into and through mechanical tensioner. The pivotally mounted guide frame 132 is spring biased about the mounting pin 142 to pivot the top pivotal frame away from the top of stationary frame 130, such that the suture extending between the guide elements of frames 130 and 132 is placed under tension while being pulled therethrough.

The suture 102 then extends to and is wrapped around tension roller 134. As mentioned above, roller 134 is mounted on one end of torque motor 136, which applies a given tension to the suture as it is pulled through the suturing assembly by grippers 92 and 94. From tension roller 134, suture 102 extends to an out-of-suture sensor 146, and then through a pair of opposed rollers of a knot detector 150. One of these rollers is mounted on one end of a lever arm, and if a knot travels between this pair of opposed rollers, it pushes the lever arms away, and this movement of the lever arms is detected by a photodetector.

The suture 102 then travels around an idler roller 152 to change direction, to a further idler roller 154 to change direction again, and through tipping assembly 96. The suture then extends downwardly from the tipping assembly to an idler roller 156, mounted near the bottom of the drawing frame, at which the suture reverses direction and travels vertically upwardly to the gripper assemblies.

Motor controller 138, preferably, is a control processing logic unit, and is provided to control motor 136. Brake 140 is provided to brake motor 136 whenever machine 10 detects a suture break or a fatal alarm condition, and the brake prevents the motor from pulling suture 102 in a direction opposite its intended direction of movement and entangling or wrapping the suture in the motor or the tensioning mechanism.

Figure 7:
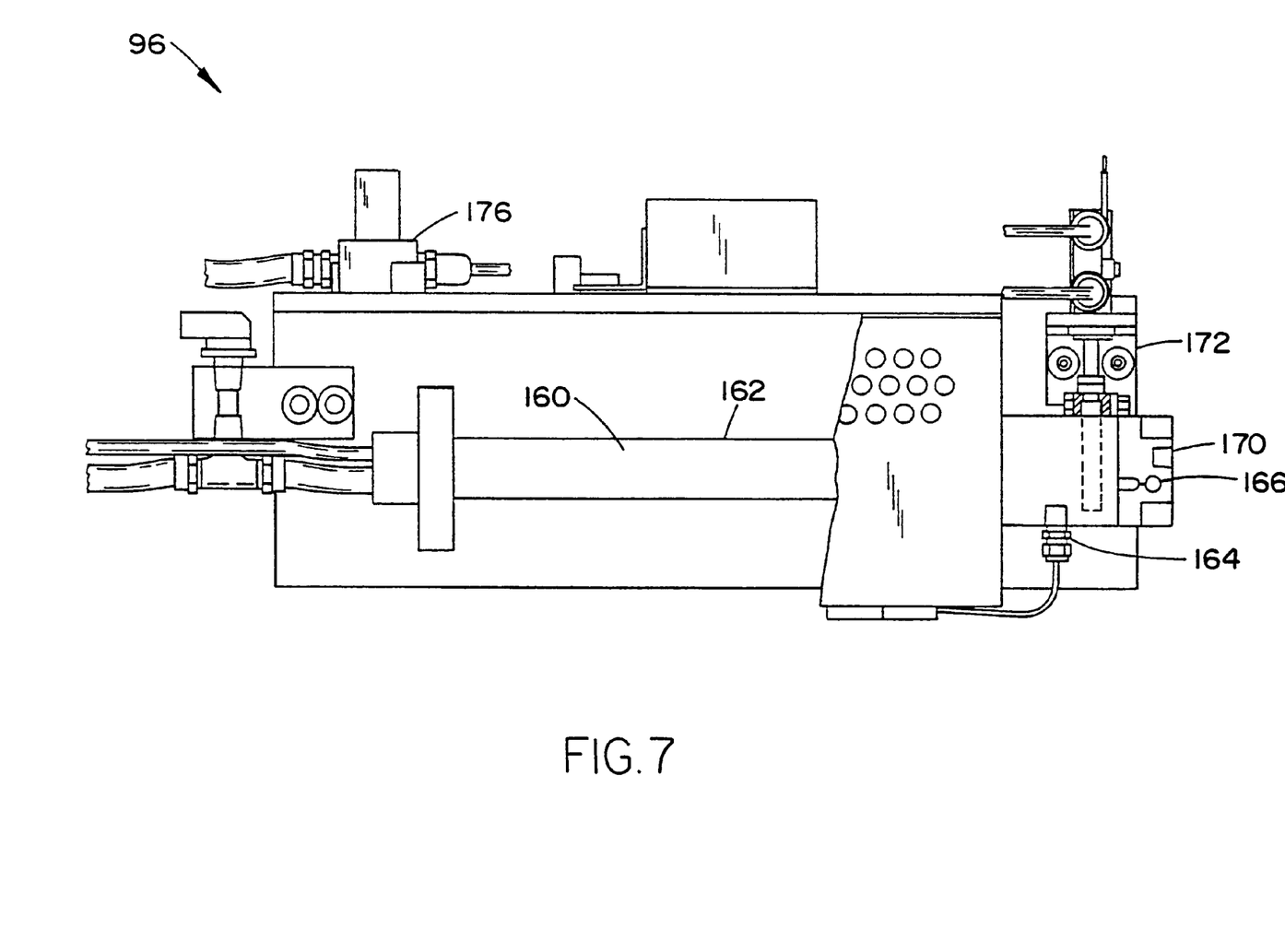
FIG. 7 shows a tipping assembly of the suturing station.

The tipping assembly 96 is shown in detail in FIG. 7; and this assembly operates by flowing air, supplied at a regulated pressure and flow rate, over a heater coil 160 mounted within an outer heater casing 162. A thermocouple 164 is positioned in the air flow at the discharge end of the heater casing 162 to monitor and control the air temperature through a controller in a programmable logic controller. The tipping assembly 96 is operated at various temperatures between 200° F. and 550° F., depending upon the particular suture material being used on machine 10. The particular temperature is a down loaded parameter from an operating program at each suture batch change over.

The constant flow of heated air at the outlet of 162 either (1) flows through the heating aperture 166 in which the suture 102 is intermittently stopped and positioned during a tipping operation, or alternatively (2) is conducted into the surrounding atmosphere through a diverter channel 170. The flow of hot air is controlled by an air cylinder 172, under control of a solenoid 176. The air cylinder 172 controls the position of a retractable slide element having a flow aperture therein which is selectively positioned in front of either a channel into the heating aperture 166, or the diverter channel 170.

Figure 8:
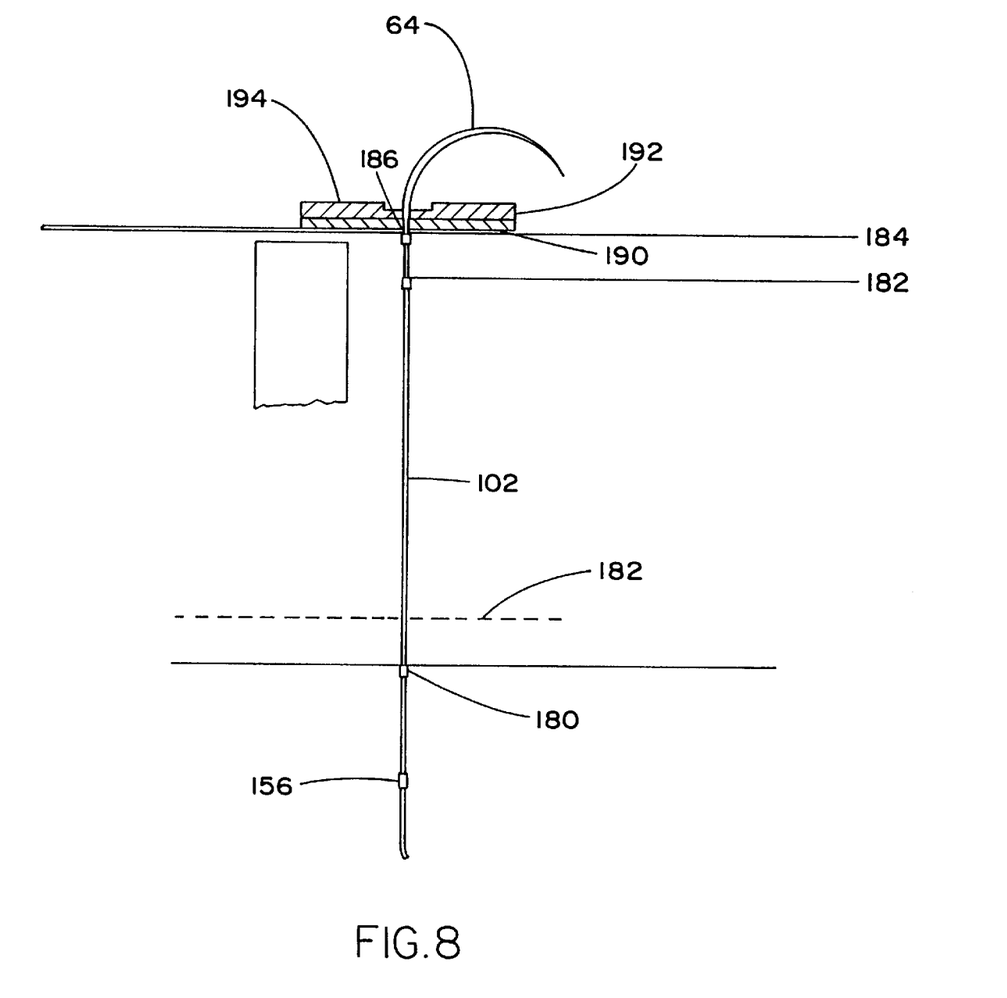
FIG. 8 is a diagrammatic illustration of various parts and positions of the suturing station.

FIG. 8 is a schematic illustration of various elements and positions including, from the bottom, the idler roller 156, a bottom servo gripper position 180, the position 182 of a cutting blade, the home position 182 of the servo gripper, and the final insertion position 184 of the servo gripper. During operation, a gripper assembly stops at a home position and waits a predetermined time, during which a needle is preclamped in an insertion position in the swaging station. The gripper assembly then inserts the suture end into the needle.

During this insertion step, the cut suture end is guided by a funnel shaped aperture 186 in a funnel element into an aperture in the end of the needle. The bottom gripper assembly then closes, a tipping operation is performed simultaneously at the tipping assembly 96, and a swage die is simultaneously actuated to swage the needle end around the suture, attaching it thereto. In particular, a moving anvil 192 is moved relative to a stationary anvil 194 of the swage die to swage and attach the needle to the suture. Thereafter, the cutting assembly 100 is activated, to cut the stiffened area of the suture, thereby to cut the suture to the desired length. Then, the upper gripper assembly opens, that upper gripper assembly returns to a bottom position, and simultaneously therewith the lower gripper assembly moves up to the home position, and the cycle is then repeated.

As mentioned above, machine 10 may be used with a variety of types and sizes of needles and suture materials, and typically, it is desirable to adjust one or more of the parameters on the machine whenever the needle/suture combination is changed. More specifically, each possible combination of materials has a respective set of parameters associated with it, and preferably a multitude of such sets of parameters, referred to as batch recipes, are stored in the memory of supervisor computer 62. When the type of needle or the type of suture used in machine 10 is changed, an operator inputs information to computer 60 identifying the new needle/suture combination, and this information is transmitted to supervisor computer 62. When this is done, the appropriate batch recipe is then downloaded to the mechanisms and assemblies of machine 10; and more specifically, the parameters of the recipe are transmitted to the appropriate elements or assemblies of the machine.

Among the parameters that may be changed at work station 30 are the depth to which the suture tip is inserted into the needle, the dwell time of the suture at the tipping assembly 96, the length of time the suture is cooled after being heated at that tipping assembly, and the tension applied to the suture 102 by tensioning mechanism 90. The proper suture tension is important because, among other reasons, it helps the cutting assembly achieve a clean, neat cut on the suture, a type of cut referred to as a broom free cut.

When a batch recipe is downloaded from supervisor computer 62, values for the suture insertion depth and the suture cooling time are transmitted to the control processing logic units 124 and 126, and the value for the desired suture tension is transmitted to the control processor logic unit 138 of the tensioning mechanism 90.

With reference to FIGS. 4 and 8, to adjust the depth to which the suture is inserted into the needle, the operation of motors 114 and 116 may be adjusted to increase or decrease the height to which gripper arms 92 and 94 are driven during the suture insertion step. For example, these motors may be operated longer during this step to move the grippers further upward, with the specific length of operation being determined by a value transmitted to control processing unit from the relevent batch recipe.

To increase the length of time the suture is cooled after being heated by tipping assembly 96, motor controllers 124 and 126 may delay operation of the motors 114 and 116 to delay movement of the gripper assemblies 92 and 94. For example, the gripper assemblies may be held for a longer period of time at the home position, at the insert position, or at some other position in the path of movement of the grippers. The specific length of that delay is determined by a value transmitted to controllers 124 and 126 from supervisor computer 62.

Figure 9:
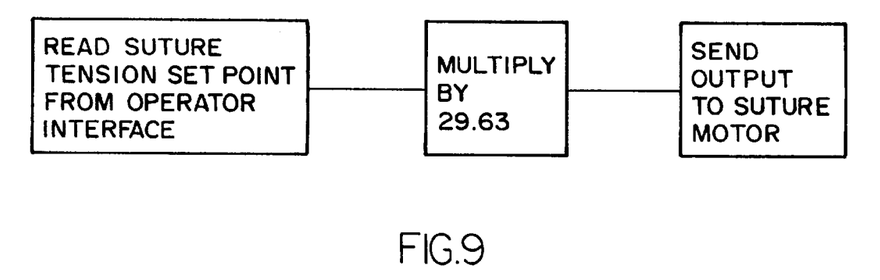
FIG. 9 is a flow diagram illustrating how the motor of the tensioning mechanism of FIG. 6 is adjusted to vary the tension applied to the suture.

In order to allow the tension on suture 102 to be changed, the torque that motor 136 applies to tension roller 134 is adjustable, and preferably motor 136 is a variable torque motor. As schematically illustrated in FIG. 9, whenever a batch recipe is downloaded to machine 10, a value is transmitted to processing logic unit 138 indicating the appropriate torque to be applied to tension roller 134, and this logic unit then operates motor 136 to apply that torque to the tension roller. This motor controller 138 may convert the data transmitted to it to another value or format that is used directly to operate the motor.

In addition to the foregoing, preferably the motor controller unit 138 continuously monitors operation of machine 10 and continuously determines whether the motor 136 is to run or stop. More specifically, preferably motor 136 is of the type that requires that a run or operate signal be applied to the motor in order for the motor to operate, and if that signal is not applied to the motor, the motor stops. The motor controller 138 continuously monitors a number of factors and, on the basis of those factor, transmits, or does not transmit, a run signal to the motor 136, causing the motor, respectively, to operate or to not operate. Also, preferably, if the controller 138 determines that motor 136 should not be operating, then a signal is applied to brake 140 to operate the brake to brake motor 136 to prevent or to inhibit the momentum of the motor from undesirably rotating roller 134.

Figure 10:
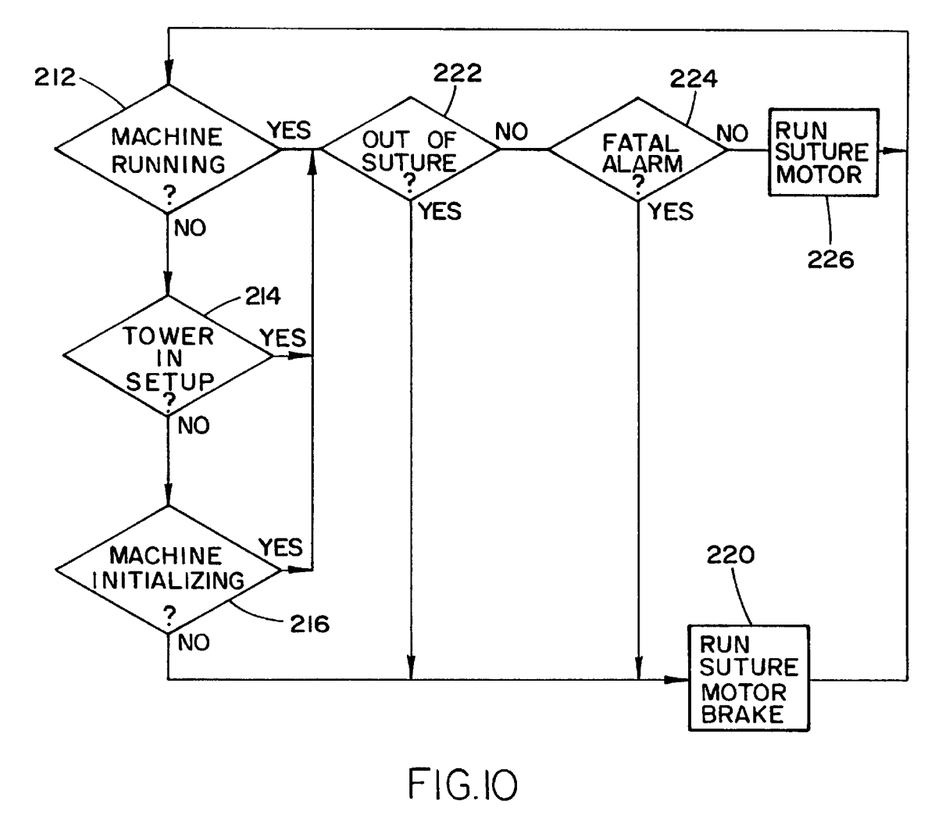
FIG. 10 is a flow diagram illustrating a procedure for controlling the operation of the motor of the tensioning mechanism.

FIG. 10 shows an example of a procedure or routine that may be used to determine whether the motor run signal should be transmitted to motor 136. Steps 212, 214 and 216 in this routine are to determine, respectively, whether the machine 10 is running or operating, whether the drawing tower 80 is in a set-up mode, and whether the machine 10 is in an initialization mode.

A variety of specific procedures may be employed to make these determinations. For example, commonly with machines of the type shown in FIG. 1, the machine is prevented from operating until an operator inputs an operate enable command to computer 60; and once that is done, the machine is considered to be operating.

In addition, typically these machines have an initialization mode, in which various adjustments are made, both manually and automatically, to the machine. For example, during an initialization mode, a batch of needles may be sutured, swaged, and pull-tested to determine whether the swaging process is working properly; and if the process is not working as it should, adjustments may be made to the process. Here too, with machines of the general type shown in FIG. 1, in order to put the machine in the initialization mode, the operator inputs an appropriate command to computer 60; and when that initialization enable command is input, the machine is considered to be in the initialization mode.

The drawing tower 80 also has its own set-up mode in which, for example, suture may be installed in the tower and various other adjustments may be made. To allow this to be done, the operator inputs a tower-set-up command to computer 60; and when that command is input, the tower is considered to be in the set-up mode.

With reference to FIG. 10, if all three of conditions at steps 212, 214 and 216 are not met, then the motor run signal is not sent to motor 136, and instead, a signal is sent to motor brake 140 to brake the motor, as represented by step 220. However, if any one of the conditions at steps 212, 214 and 216 is satisfied, the routine proceeds to step 222, where a test is made to determine whether drawing tower is out of suture. Any suitable procedure may be used to perform this test. For instance, with the preferred embodiment of drawing tower shown in FIGS. 4 and 5, 146 sensor is used to determine whether or not the tower has suture. More specifically, if this sensor detects suture, then the tower is considered to have suture; while if sensor does not detect suture, then the tower is considered to be out of suture. If the drawing tower is determined to be out of suture, the motor run signal is not sent to the motor, and instead, a signal is sent to motor brake to operate that brake.

If, in contrast, at step 222, a determination is made that the drawing tower has suture, then the routine proceeds to step 224, where a check is made to determine whether any of a number of conditions, generally referred to as fatal alarm conditions, has been detected. To elaborate, with machines of the general type shown in FIG. 1, a number of sensors are used to monitor and check for a plurality of predefined conditions that, if one occurs, would be a reason for stopping the machine.

If, at step 224, one of these fatal alarm conditions is present, the motor run signal is not transmitted to motor 136, and instead a signal is transmitted to brake 140 to brake the motor, If, however, the routine reaches step 224 and no fatal alarm condition is detected, then the motor run signal is transmitted to motor 136, as represented by step 226, causing the motor to operate or to continue to operate. From step 226, or step 220, the routine returns to step 212, and the routine is repeated. Preferably the routine is repeated on a continuous, regular basis; and, for example, the routine may be repeated every second.

While it is apparent that the invention herein disclosed is well calculated to fulfill the objects previously stated, it will be appreciated that numerous modifications and embodiments may be devised by those skilled in the art, and it is intended that the appended claims cover all such modifications and embodiments as fall within the true spirit and scope of the present invention.

We claim:

1. A system for applying a predetermined, given tension to different size and/or type sutures, the system comprising:
    a rotatable roller for engaging a particular size and/or type suture being tensioned;
    a variable torque device connected to the roller to apply a given torque thereto to resist rotation of the roller resulting in the application of the given tension to the particular size and/or type suture being tensioned; and
    a control subsystem including
        i) means to identify the given torque level which results in the given tension for the particular size and/or type suture being tensioned, and
        ii) a controller to operate the variable torque device to apply the given torque level to the roller.

2. A system according to claim 1, wherein the means to identify the given torque level includes:
    a memory area storing a multitude of values representing different torque levels;
    means to identify one of said multitude of values; and
    means to transmit to the controller a signal representing the identified one of said values.

3. A system according to claim 1, wherein the variable torque device is a motor.

4. A method for applying a predetermined, given tension to different size and/or type sutures, the method comprising the steps of:
    wrapping a particular size and/or type suture being tensioned around a rotatable roller;
    using a variable torque device to apply a given torque to the roller to resist rotation of the roller resulting in the application of the given tension to the particular size and/or type suture being tensioned;
    identifying the given torque level which results in the given tension for the particular size and/or type suture being tensioned; and
    operating the variable torque device to apply the given torque level to the roller.

5. A method according to claim 4, wherein the step of identifying the given torque level includes the steps of:
    storing in a memory area a multitude of values representing different torque levels;
    identifying one of said multitude of values;
    transmitting to a controller a signal representing the identified one of said values; and
    using the controller to control the variable torque device to apply the given torque level to the roller.

6. A system for inserting a suture into different size needles to a predetermined, given depth for each particular size needle in which the suture is being inserted, the system comprising:
    a gripper assembly for holding the suture;
    means movably connected to the gripper assembly;
    moving means connected to the gripper assembly to move said assembly a controlled distance such that the suture is inserted the given depth into the particular size needle; and
    a control subsystem including;
        i) means to identify said given depth for the particular size needle in which the suture is being inserted, and
        ii) a controller to operate the moving means to move the gripper assembly to move the suture to said given depth in the particular size needle in which the suture is being inserted.

7. A system according to claim 6, wherein the means to identify the given depth includes:
    a memory area storing a multitude of values representing different depth positions;
    means to identify one of said multitude of values; and
    means to transmit to the controller a signal representing the identified one of said values.

8. A system according to claim 7, wherein:
    the gripper assembly has a defined, stationary home position on the supporting means; and
    the moving means moves said assembly said controlled distance from the home position to insert the suture into the needle.

9. A system according to claim 7, wherein:
    the moving means is a motor;
    the controller operates the motor different lengths of time to insert the suture to different depths in the needle;
    each of said multitude of values is associated with one of a plurality of lengths of times; and
    the controller operates the motor the length of time associated with the identified one of said multitude of values to insert the suture to said given depth in the needle.

10. A method for inserting a suture into different size needles to a predetermined, given depth for each particular size needle in which the suture is being inserted, the method comprising the steps of:
    gripping the suture with a gripper assembly;
    using a moving device to move the gripper assembly a controlled distance such that the suture is inserted the given death into the particular size needle;
    identifying the given depth for the particular size needle in which the suture is being inserted; and
    operating the moving device to move the gripper assembly to move the suture to the given depth in the particular size needle in which the suture is being inserted.

11. A method according to claim 10, wherein the step of identifying the given depth includes the steps of:
    storing in a memory area a multitude of values representing different depth positions;
    identifying one of said multitude of values;
    transmitting to a controller a signal representing the identified one of said values; and
    using the controller to control the moving means to move the suture to said given depth in the needle.

12. A method according to claim 11, wherein:
    the using step includes the step of using a motor to move the gripper assembly to insert the suture into the needle;
    the controller operates the motor different lengths of time to insert the suture to different depths in the needle;

each of said values is associated with one of a plurality of lengths of time; and the operating step includes the step of operating the motor the length of time associated with the identified one of said multitude of values to insert the suture to said given depth in the needle.

13. A system for cooling different size and/or type sutures for a predetermined, given length of time for each particular size and/or type suture being cooled, the system comprising:

means for heating and then cooling a particular suture for its given length of time; and a control subsystem including
 i) means to identify the given length of time for the particular size and/or type suture being cooled, and
 ii) a controller to operate the heating and cooling means to cool the particular size and/or type suture being cooled for its given length of time.

14. A system according to claim 13, wherein the means to identify the given length of time includes:

a memory area storing a multitude of values representing different lengths of time;

means to identify one of said values; and means to transmit to the controller a signal representing the identified one of said values.

15. A method for cooling different size and/or type sutures for a predetermined, given length of time for each particular size and/or type suture being cooled, the method comprising the steps of:

heating and then cooling the a particular suture being cooled for its given length of time;

using a controller to cool the particular suture being cooled for its given length of time;

identifying the given length of time for the particular size and/or type suture being cooled; and operating the controller to cool the particular size and/or type suture being cooled for its given length of time.

16. A method according to claim 15, wherein the step of identifying the given length of time, includes the steps of:

storing in a memory area a multitude of values representing different lengths of time;

identifying one of said multitude of values; and transmitting to the controller a signal representing the identified one of said values.

17. A system for varying parameters at a needle suturing station of the type wherein a plurality of operations are performed on different size and/or type sutures, to insert a particular size and/or type suture into the needle and to swage the needle to the particular size and/or type suture, and wherein each individual operation in the plurality of operations includes a set of parameters associated with each particular size and/or type suture, the system comprising:

a plurality of controllers, each of the controllers controlling a respective one of said parameters;

a memory area holding sets of values, each of the sets having a respective one value for each of said parameters;

means to transmit said sets of values to the controllers; and including means to transmit to each of the controllers, when one of said sets of values is transmitted to the controllers, the one value in said one set for the parameter controlled by said controller.

18. A method for varying parameters at a needle suturing station of the type wherein a plurality of operations are performed on different size and/or type sutures, to insert a particular size and/or type suture into the needle and to swage the needle to the particular size and/or type suture, and wherein each individual operation in the plurality of operations includes a set of parameters associated with each particular size and/or type suture, the method comprising the steps of:

using a plurality of controllers to control the parameters, wherein each of the controllers controls a respective one of said parameters;

holding in a memory area sets of values, each of the sets holding a respective one value for each of the parameters; and transmitting said sets of values to the controllers, including the step of, when one of said sets is transmitted to the controllers, transmitting to each of the controllers the one value in said set for the parameter controlled by the controller.

19. A method according to claim 18, wherein said parameters include a suture tension.

20. A system for controlling a motor for applying tension to a suture at a needle suturing station in an automated needle suturing machine, the system comprising:

means to generate operate signals; and means to transmit the operate signals to the motor under predetermined conditions to operate the motor to apply tension to the suture;

wherein the station and the machine have a plurality of defined operating modes, and the means to transmit includes means for transmitting the operate signals to the motor only when the station and the machine are in any one of a predetermined set of defined operating modes.

21. A system according to claim 20, wherein the means to transmit includes means to sense for a group of alarm conditions and to generate an alarm signal when any one of the alarm conditions is sensed; and the means to transmit does not transmit the operate signal to the motor when the alarm signal is generated.

22. A method for controlling a motor for applying tension to a suture at a needle suturing station in an automated needle suturing machine, comprising the steps of:

generating operate signals; and transmitting the operate signals to the motor under predetermined conditions to operate the motor to apply tension to the suture;

wherein the station and the machine have a plurality of defined operating modes, and the transmitting step includes the step of transmitting the operate signals to the motor only when the station and the machine are in any one of a predetermined set of the defined operating modes.

23. A method according to claim 22, wherein the transmitting step further includes the steps of:

sensing for the presence of suture at the suturing station;

generating a suture present signal when suture is sensed at the suturing station; and only transmitting the operate signals to the motor when the suture present signal is generated.

24. The system according to claim 20, wherein the means to transmit includes means to sense for the presence of suture and to generate a suture present signal when suture is sensed; and wherein the means to transmit only transmits the operate signal to the motor when the suture present signal is generated.

* * * * *

UNITED STATES PATENT AND TRADEMARK OFFICE
CERTIFICATE OF CORRECTION

PATENT NO. : 5,920,482
DATED : July 6, 1999
INVENTOR(S) : D. Demarest et al.

It is certified that error appears in the above-identified patent and that said Letters Patent is hereby corrected as shown below:

Column 7,
Line 36, "relevent" should read -- relevant --

Column 9, claim 1,
Lines 17-30, delete claim 1, insert:
-- 1. A system for applying a predetermined, given tension to one of a plurality of different size and/or type sutures capable of being tensioned, the system comprising:
 a rotatable roller for engaging a particular size and/or type suture being tensioned;
 a variable torque device connected to the roller to apply a given torque thereto to resist rotation of the roller resulting in the application of the given tension to the particular size and/or type suture being tensioned; and a control subsystem including
 i) means to identify and output the given torque level which results in the given tension for the particular size and/or type suture being tensioned, and
 ii) a controller to automatically operate the variable torque device in response to said output to apply the identified given torque level to the roller. --

Column 9 & 10, claim 4,
Lines 40-53, delete claim 4, insert:
-- 4. A method for applying a predetermined, given tension to one of a plurality of different size and /or type sutures capable of being tensioned, the method comprising the steps of:
 wrapping a particular size and/or type suture being tensioned around a rotatable roller;
 using a variable torque device to apply a given torque to the roller to resist a rotation of the roller to resist rotation of the roller resulting in the application of the given tension to the particular size and/or type suture being tensioned;
 identifying and outputting the given torque level which results in the given tension for the particular size and/or type suture being tensioned; and
 operating the variable torque device automatically in reponse to said output to apply the identified given torque level to the roller. --

Column 9, claim 6,
Lines 40-53, delete claim 6, insert:
-- 6. A system for inserting a surture into one of a plurality of different size needles capable of being processed to a predetermined, given depth for each particular size needle in which the suture is being inserted, the system comprising:
 a gripper assembly for holding the suture;
 means connected to the gripper assembly;
 moving means connected to the gripper assembly to move said assembly a controlled distance such that the suture is inserted the given depth into the particular

UNITED STATES PATENT AND TRADEMARK OFFICE
CERTIFICATE OF CORRECTION

PATENT NO. : 5,920,482
DATED : July 6, 1999
INVENTOR(S) : D. Demarest et al.

It is certified that error appears in the above-identified patent and that said Letters Patent is hereby corrected as shown below:

size needle being processed; and a control subsystem including;

i) means to identify and output said given depth for the particular size needle in which the suture is being inserted, and ii) a controller to automatically operate the moving means in response to said output to move the gripper assembly to move the suture to said indentified given depth in the particular size needle in which the suture is being inserted. --

Column 10, claim 10,
Lines 39-53, delete claim 10, insert:
-- 10. A method for inserting a suture into one of a plurality of different size needles capable of being processed to a predetermined, given depth for each particular size needle in which the suture is being inserted, the method comprising the steps of:
gripping the suture with a gripper assembly;
using a moving device to move the gripper assembly a controlled distance such that the suture is inserted the given depth into the particular size needle being processed;
identifying and outputting the given depth for the particular size needle in which the suture is being inserted; and
operating the moving device automatically in response to said output to move the gripper assembly to move the suture to the identified given depth in the particular size needle in which the suture is being inserted. --

Column 11, claim 13,
Lines 7-18, delete claim 13, insert:
-- 13. A system for cooling one of a plurality of different size and/or sutures capable of being cooled for predetermined, given length of time for each particular size and/or type suture being cooled, the system comprising:
means for heating and then cooling a particular suture for its given length of time; and conntrol subsystem including
i) means to identify and output the given length of time for the particular size and/or type suture being cooled, and
ii) a controller to automatically operate the heating and cooling means in response to said output to cool the particular size and/or type suture being cooled for its identified given length of time. --

Column 11, claim 15,
Lines 26-38, delete claim 15, insert:
-- 15. A method for cooling one of a plurality of different size and/or type sutures capable of being cooled for a predetermined, given length of time for each particular size and/or type suture being cooled, the method comprising the steps of:
heating and then cooling a particular suture being cooled for its given length of time;

UNITED STATES PATENT AND TRADEMARK OFFICE
CERTIFICATE OF CORRECTION

PATENT NO. : 5,920,482
DATED : July 6, 1999
INVENTOR(S) : D. Demarest et al.

It is certified that error appears in the above-identified patent and that said Letters Patent is hereby corrected as shown below:

identifying and outputting the given length of time for the particular size and/or type suture being cooled; and operating the controller automatically in response to said output to cool the particular size and/or type suture being cooled for its identified given length of time. --

Column 11, claim 17,
Lines 26-38, delete claim 17, insert
-- 17. A system for varying parameters at a needle suturing station of the type wherein a plurality of operations are performed on one of a plurality of different size and/or type sutures capable of being processed, to insert a particular size and/or type suture into the needle and to swage the needle to the particular size and/or type suture, and wherein each individual operation in the plurality of operations includes a set of parameters associated with each particular size and/or type suture, the system comprising:

a memory area holding identified sets of values, each of the sets having a respective one value for each of said parameters for each particular type and/or size suture to be processed;

a plurality of controllers, each of the controllers automatically controlling a respective one of said parameters in response to the indentified set of values;

means transmit said identified set of values to the controllers; and including means to transmit each of the controllers the one value in said one set for the parameter controlled by said controller. --

Column 11 & 12, claim 18,
Line 65-78, delete claim 18, insert:
-- 18. A method for varying parameters at a needle suturing station of thetype wherein a plurality of operations are performed on one of a plurality of different size and/or type sutures capable of being processed, to insert a particular size and/or type suture into the needle and to swage the needle to the particular size and/or type suture, and wherein each individual operation in the plurality of operations includes a set of parameters associated with each particular size and/or type suture, the method comprising the steps of:

holding in a memory area identified sets of values, each of the sets holding a respective one value for each of the parameters for the particular size and/or type suture being processed;

using a plurality of controllers to automatically control the parameters, wherein each of the controllers controls a respective one of said parameters in response to the identified set of values; and transmitting said identified set of values to the controllers to each of thecontrollers the one value in said set for the parameter controlled by the controller. --

UNITED STATES PATENT AND TRADEMARK OFFICE
CERTIFICATE OF CORRECTION

PATENT NO. : 5,920,482
DATED : July 6, 1999
INVENTOR(S) : D. Demarest et al.

It is certified that error appears in the above-identified patent and that said Letters Patent is hereby corrected as shown below:

Column 12, claim 20,
Lines 21-33, delete claim 20, insert:
-- 20. A system for controlling a motor for applying tension to one of a plurality of sutures capable of being tensioned at a needle suturing station in an automated needle suturing machine, the system comprising:

a rotatable roller for engaging a particular size and/or type suture being tensioned;

a variable torque device connected to the roller to apply a given torque thereto to resist rotation of the roller resulting in the application of the given tension to the particular size and/or type suture being tensioned; a control subsystem including     i) means to identify and output the given torque level which results in the given tension for the particular size and/or type suture being tensioned, and     ii) a controller to automatically operate the variable torque device in response to said output torque level to apply the identified given torque roller;

means to generate and output operate signals; and means to transmit the operate signals to the motor under predetermined conditions to automatically operate the motor in response to the output operate signal to apply tension to the particular suture being tensioned;

wherein the station and the machine have a plurality of defined operating modes, and the means to transmit includes means for the transmitting the operate signal to apply tension to the particular suture being tensioned;

wherein the station and the machine have a plurality of defined operating modes, and the means to transmit includes means for transmitting the operate signals to the motor only when the station and the machine are in any one of predetermined set of defined operating modes. --

Signed and Sealed this

Eighteenth Day of December, 2001

*Attest:*

*Attesting Officer*

JAMES E. ROGAN
*Director of the United States Patent and Trademark Office*